United States Patent [19]

Fahim

[11] 4,357,934

[45] Nov. 9, 1982

[54] METHOD OF TREATING MALE INFERTILITY

[75] Inventor: Mostafa S. Fahim, Columbia, Mo.

[73] Assignee: The Curators of the University of Missouri, Columbia, Mo.

[21] Appl. No.: 171,498

[22] Filed: Jul. 23, 1980

[51] Int. Cl.³ .............................................. A61M 5/00
[52] U.S. Cl. .................................... 128/1 R; 128/79; 424/243
[58] Field of Search .................. 128/79, 1 R; 424/243

[56] References Cited

U.S. PATENT DOCUMENTS 4,156,427  5/1979  Fahim ................................ 128/215

OTHER PUBLICATIONS

Local Male Hormonal Therapy in Male Infertility, A Prelim. Report, Fahim, M. S., Arch Androl., vol. 3, No. 2, 1979, pp. 181–184.

Hawley (ed.), Condensed Chemical Dictionary, 9th ed., van Nostrand, pp. 445 & 844.

Primary Examiner—Kyle L. Howell
Assistant Examiner—Nancy A. B. Swisher
Attorney, Agent, or Firm—Grace J. Fishel

[57] ABSTRACT

Male infertility is treated by increasing the concentration of testosterone in the seminiferous tubules by intratesticular injection of an aqueous suspension of testosterone and/or chorionic gonadotropins without correspondingly increasing the testosterone level in the blood plasma and thereby without substantially interfering with the secretion of the gonadotropins FSH and LH by the pituitary.

12 Claims, No Drawings

METHOD OF TREATING MALE INFERTILITY

The present invention relates to a method for treating normogonadotropic idiopathic oligospermia and asthenospermia in males.

It is generally accepted that the continued secretion by the pituitary gland of the gonadotropins, follicle stimulating hormone (FSH) and luteinizing hormone (LH), is responsible for the development and maintenance of spermotogenesis and for the development and subsequent functional maintenance of the testicular interstitial or Leydig cells. It is also generally accepted that ther is an endocrine feedback system between the pituitary gland and the testes.

In the past, testosterone and/or gonadotropins have been administered systemically, usually by intramuscular injection, in the treatment of male infertiliy. Such administration, however, usually increases the plasma level of testosterone which suppresses further release of the gonadotropins by the pituitary. Hence even though the testosterone level in the seminiferous tubules may be increased, the gonadotropins necessary for sperm cell maturation are decreased. The net effect of such systemic treatments varies from patient to patient and is very difficult to control.

In view of the above, it is an object of the present invention to provide a method for treating male infertility by increasing the concentration of testosterone in the seminiferous tubules without correspondingly increasing the testosterone level in the blood plasma. Other objects and features will be in part apparent and in part pointed out hereinafter. The invention accordingly comprises the method of treatment hereinafter described, the scope of the invention being indicated by the subjoined claims.

For the purpose of the present invention, the testosterone and human chorionic gonadotropin (hCG) must be administered intratesticularly in a form which will penetrate the blood-testis barrier without rupturing the seminiferous tubules and without dispersing substantial amounts of the suspended hormones into the blood plasma. Accordingly, a testosterone and/or chorionic gonadotropin suspension is prepared by suspending the hormones in a sterile aqueous solution containing an antimicrobial preservative such as thimerosal and a buffering salt, preferably sodium phosphate, to maintain a pH in the range 6.5 to 7.5, preferably 6.8. Since the hormones are water insoluble, suitable suspending or dispersing agents such as sodium carboxymethyl cellulose, polyvinylpyrrolidone, dioctyl sodium sulfosuccinate or the like must also be included.

For the comfort of the patient and to avoid possible rupture of the seminiferous tubules because of the injection, the volume of fluid injected into each testis of a human male should be no more than 1.5 ml, and is preferably in the range from 0.25 to 1 ml, most preferably about 0.5 ml. So that a 0.5 ml dose will contain an effective amount of testosterone and/or chorionic gonadotropin, the above-mentioned suspensions should be prepared from 5 to 50 mg/ml of testosterone, preferably about 30 mg/ml, or from 1 to 20 IU of hCG, preferably about 10 IU. When the suspension contains both hormones, the water preferably contains from 20 to 30 mg/ml testosterone and 5 to 20 IU hCG, most preferably 30 mg/ml testosterone and 10 IU hCG. Since the hormones are water insoluble, it is preferred to dissolve them in a small amount of glycerol such that the suspension will contain about 2% by volume glycerol. While the amount of suspending or dispersing agent will ultimately depend on the nature of the agent, suitable testosterone and/or hCG suspensions are prepared containing 1 to 5 mg/ml sodium carboxymethyl cellulose, 0.1 to 0.4 mg/ml polyvinylpyrrolidone and 0.1 to 0.2 mg/ml dioctyl sodium sulfosuccinate.

Sperm quality is measured in terms of density, motility and morphology and certain minimal requirements for the likelihood of fertilization are generally accepted: an ejaculate volume of 1.5 to 5 ml; a sperm density of greater than 20 million/ml, 60% of which should exhibit vigorous motility (i.e., quality of movement, which should be purposeful and forward) at less than 2 hours after ejaculation; a sperm viability (i.e., sperm that are "moving" at time of inspection) of greater than 60%; and less than 40% abnormal morphologic forms. The terms oligospermia and asthenospermia are somewhat empirical but as used herein, oligospermia is used to describe the condition of those patients whose sperm count before treatment was less than 50 million/ml and asthenospermia is applied to the condition of those with a count below about 1 million/ml.

Before a patient is treated, his condition should be diagnosed as normogonadotropic idopathic oligospermia or asthenospermia to rule out the many other possible causes for male infertility. His scrotum should be cleaned with a disinfectant and the needle sterilized as the testes are very susceptible to infection. The selected testis should be palpated and the head and tail of the epididymis located. The injection is then given through the tunica albuginea into the midline of the testis. It is important that the injection not be given near the head of the epididymis so that the blood vessels are avoided as they enter the testis and it is also important that the injection not be given in the tail of the epididymis to avoid granuloma.

In general, oligospermia or asthenospermia are usually accompanied by low levels of sperm motility. While the best response to treatment in accordance with the present invention results in increases in density and motility, this does not always occur. Sometimes only the motility is improved but this improvement alone may result in increased fertility as proved by pregnancy. In mild cases of oligospermia, the suspension need only contain testosterone but in more severe cases, it is preferred to use a combination of testosterone and hCG. While the function of the hCG is not entirely understood, it is believed to function somewhat like LH in stimulating spermatogenesis.

If necessary, treatment may be repeated, preferably at three-month intervals since that is the time necessary for a complete cycle of spermatogenesis from spermatogonia, spermatocytes and spermatids to mature sperm. If impregnation has occurred in the meanwhile, no further treatment may be necessary or desired.

The following examples illustrate the invention.

EXAMPLE 1

Eighteen infertile patients suffering from severe oligospermia with ages between 26 and 45 years with a mean of 34 years were treated in accordance with the present invention. All of the patients had primary sterility with marital duration varying from 2 to 20 years with a mean of 6.6 years and no progeny. All had general good health, well-developed secondary characteristics, no apparent endocrine disturbances and no sexual complaints. Semen showed severe oligospermia with counts below 6 million/ml associated with impaired motility in 9 cases and necrospermia in the remaining 9 cases. In 15 cases, local intratesticual injection was done after taking a testicular biopsy through the same opening in the tunica albuginea. In the remaining 3 cases, injection was done after infiltration of the cord and the subcutaneous tissue by local anesthetics. The injection material used was a sterile aqueous testosterone suspension consisting of 50 mg/ml testosterone (17-beta-hydroxy-4-androsten-3-one), 2 mg/ml sodium carboxymethyl cellulose, 0.3 mg/ml polyvinylpyrrolidone, 0.15 mg/ml dioctyl sodium sulfosuccinate and 0.08 mg/ml thimerosal as a preservative. In all cases, 0.5 ml was used to infiltrate each testis. Testicular biopsy was obtained before treatment. Semen examination was done before and 3 months after the local injection.

In all cases, there were no postoperative complications or testicular discomfort. No ill effects were reported by the patients presenting themselves for a second examination 3 months after the injection, and local examination of the scrotum showed no changes. Potency was reported as increased in seven patients and as no change in the remaining patients.

Semen analysis 3 months after the injection showed that 8 cases improved in varying degrees. Both density and motility increased in 4 cases, while density alone increased in another 2 cases and motility alone improved in the remaining 2 cases. Correlation between testicular biopsy and semen showed that responding cases were those with biopsies showing mild changes, such as sloughing, hypercellularity and partial spermatogenic arrest; 50% of such cases responded favorably. Cases with degenerative changes such as tubular hyalinization as well as cases showing spermatogenic arrest at early stages showed no response. The results are reported in Table I below.

TABLE I

Summary of Semen Analysis before and after Intratesticular Injection

| Case No. | Semen Analysis Before Injection | | | Semen Analysis After Injection | | | Response |
|---|---|---|---|---|---|---|---|
| | Density | Motility | Abnormality | Density | Motility | Abnormality | |
| 1 | 5 | 20% | 40% | 4 | 30% | 40% | no response |
| 2 | 1 | 0 | 50% | 19 | 15% | 30% | improved in count and motility |
| 3 | 4 | 10% | 40% | 18 | 0 | 30% | dissociate response; count improved, motility diminished |
| 4 | 2 | 0 | 30% | 2 | 0 | 30% | no response |
| 5 | 4 | 10% | 35% | 2 | 0 | 30% | no response |
| 6 | 2 | 0 | 50% | 2 | 0 | 50% | no response |
| 7 | 4 | 20% | 30% | 19 | 30% | 30% | improved, mostly in density |
| 8 | 1 | 0 | 70% | 1 | 0 | 75% | no response |
| 9 | 2 | 0 | 70% | 2 | 0 | 60% | no response |
| 10 | 2 | 0 | 30% | 2 | 0 | 60% | no response |
| 11 | 3 | 10% | 30% | 3 | 10% | 30% | no response |
| 12 | 1 | 0 | 50% | 1 | 0 | 50% | no response |
| 13 | 6 | 15% | 30% | 4 | 40% | 20% | motility improved |
| 14 | 3 | 0 | 60% | 2 | 30% | 40% | improved in both count and motility |
| 15 | 3 | 10% | 45% | 6 | 20% | 25% | improved in both count and motility |
| 16 | 2.5 | 40% | 30% | 3 | 0 | 30% | no response |
| 17 | 3 | 20% | 20% | 5 | 30% | 20% | mild response in density and |
| 18 | 1 | 0 | 25% | 2 | 50% | 25% | motility motility improved |

Density is number of spermatoza/ml ($\times 10^6$)
Motility was analyzed 2 hours after ejaculation

EXAMPLE 2

In a colony of 120 health male dogs, six of the dogs had an average sperm count of 2 million/ml, with a range of 1 to 4 million/ml. The average sperm count of normal fertile dogs is 100 to 150 million/ml. Each testis of the six dogs was injected with 1 ml of an aqueous testosterone suspension like that described in Example 1. Sixty days after treatment, all of the dogs had normal sperm count averaging 130 million/ml.

EXAMPLE 3

A population of male rats was divided into three treatment groups, one group was the control group, one group was injected with 100 IU of hCG intramuscularly and one group was injected into each testis with an aqueous suspension like that described in Example 1 except 10 IU of hCG was substituted for the testosterone, only the last group is in accordance with the present invention, the others being for purposes of comparison. The results are reported in Table II below.

TABLE II

| Group | Sperm Count* | Motility | Testosterone Level |
|---|---|---|---|
| Control | 80 million/ml | 80% | 5.0 ng/ml |
| 1 | 20 million/ml | 20% | 20.2 ng/ml |
| 2 | 110 million/ml | 85% | 8.0 ng/ml |

*Two weeks after injection

EXAMPLE 4

Each testis of 20 infertile rats with low sperm count, 2 to 6 million/ml, and low sperm motility was injected with 10 IU hCG; then 2 weeks later, each testis of these rats was injected with 30 mg/ml testosterone in an aqueous suspension like that described in Example 1 except for the amount of testosterone. After 60 days, motility and sperm count were normal. Before this experiment was started, all 20 rats were mated with females, and no progeny occurred; however, after treatment, 18 rats impregnated females, and each female produced 7 to 10 healthy pups. The growth, sexual development and progeny of these rats were observed for three generations, and there were no genetic defects or breeding abnormalities.

In view of the above, it will be seen that the several objects of the invention are achieved and other advantageous results attained. As various changes could be made in the above method of treatment without departing from the scope of the invention, it is intended that all matter contained in the above description shall be interpreted as illustrative and not in a limiting sense.

What is claimed is:

1. A method of treating infertility in male animals by increasing the concentration of testosterone in the seminiferous tubules without correspondingly increasing the testosterone level in the blood plasma which comprises injecting a sterile aqueous suspension of testosterone into each testis of said male animal, said testosterone being suspended in an injection volume which will not rupture the seminiferous tubules.

2. The method of claim 1 wherein the aqueous suspension includes a combination of testosterone and human chorionic gonadotropin.

3. The method of claim 1 wherein the suspension contains from 5 to 50 mg/ml testosterone.

4. The method of claim 2 wherein the suspension contains from 1 to 20 IU human chorionic gonadotropin.

5. The method of claim 2 wherein the suspension contains from 20 to 30 mg/ml testosterone and from 5 to 20 IU human chorionic gonadotropin.

6. The method of claim 2 wherein the suspension contains about 30 mg/ml testosterone and about 10 IU human chorionic gonadotropin.

7. The method of claim 1 wherein the suspension additionally includes an antimicrobial preservative.

8. The method of claim 7 wherein the suspension still further includes a suspending agent or a dispersing agent.

9. The method of claim 8 wherein the suspension contains about 30 mg/ml testosterone, 10 IU human chorionic gonadotropin, 0.2 mg/ml sodium carboxymethyl cellulose, 0.15 mg/ml polyvinylpyrrolidone and 0.08 mg/ml dioctyl calcium sulfosuccinate.

10. A method of treating infertility in male animals by increasing the concentration of testosterone in the seminiferous tubules without correspondingly increasing the testosterone level in blood plasma comprising the steps of selecting a male animal having normogonadotropic idiopathic oligospermia or asthenospermia, disinfecting the skin of the scrotum, palpating the scrotum to locate the epididymis of a testis, injecting a sterile aqueous suspension of testosterone into the midline of said testis in such a way that the head and tail of the epididymis is avoided, said testosterone being suspended in an injection volume which will not rupture the seminiferous tubules.

11. The method of claim 10 wherein the animal is a human male and the volume injected into a testis is about 0.5 ml.

12. The method of claim 11 wherein the suspension contains from 20 to 30 mg/ml of testosterone and additionally from 5 to 20 IU human chorionic gonadotropin.

* * * * *